United States Patent
Khosrowshahi et al.

(10) Patent No.: US 10,188,816 B2
(45) Date of Patent: Jan. 29, 2019

(54) SYSTEM FOR REMOVING INFECTIOUS SECRETIONS

(71) Applicant: Hamid Khosrowshahi, Tarrytown, NY (US)

(72) Inventors: Hamid Khosrowshahi, Tarrytown, NY (US); Fathali Ghahremani, New York, NY (US)

(73) Assignee: Flosure Technologies LLC, Tarrytown, NY (US)

( * ) Notice: Subject to any disclaimer, the term of this patent is extended or adjusted under 35 U.S.C. 154(b) by 545 days.

(21) Appl. No.: 14/146,577

(22) Filed: Jan. 2, 2014

(65) Prior Publication Data

US 2016/0325063 A1 Nov. 10, 2016

Related U.S. Application Data

(60) Provisional application No. 61/748,487, filed on Jan. 3, 2013.

(51) Int. Cl.
| | |
|---|---|
| A61M 16/04 | (2006.01) |
| A61M 16/00 | (2006.01) |
| A61M 1/00 | (2006.01) |
| A61M 11/02 | (2006.01) |
| A61M 11/00 | (2006.01) |

(52) U.S. Cl.
CPC ...... *A61M 16/0463* (2013.01); *A61M 1/0031* (2013.01); *A61M 11/006* (2014.02); *A61M 11/02* (2013.01); *A61M 16/0009* (2014.02); *A61M 16/0434* (2013.01); *A61M 16/0479* (2014.02); *A61M 16/0484* (2014.02); *A61M 16/0486* (2014.02)

(58) Field of Classification Search
CPC .......... A61M 16/0434; A61M 16/0463; A61M 16/0465; A61M 16/0051; A61M 16/0057; A61M 11/02; A61M 1/0023; A61M 1/0031; A61M 1/0039; A61M 1/0058; A61M 1/008; A61M 1/0084
USPC .......................... 128/202.13, 202.16, 202.17
See application file for complete search history.

(56) References Cited

U.S. PATENT DOCUMENTS

| | | | | |
|---|---|---|---|---|
| 4,739,756 | A | | 4/1988 | Horn |
| 5,582,167 | A | * | 12/1996 | Joseph ................ A61M 16/044 |
| | | | | 128/207.15 |
| 5,642,730 | A | * | 7/1997 | Baran ................ A61M 16/0463 |
| | | | | 128/200.23 |
| 6,129,701 | A | * | 10/2000 | Cimino ................ A61M 1/0047 |
| | | | | 604/30 |

(Continued)

FOREIGN PATENT DOCUMENTS

| | | |
|---|---|---|
| EP | 0092618 | 11/1893 |
| EP | 0092618 A1 | 11/1983 |

*Primary Examiner* — Jan Christopher Merene
*Assistant Examiner* — Elliot S Ruddie
(74) *Attorney, Agent, or Firm* — Levisohn Berger LLP

(57) ABSTRACT

A tracheal/endotracheal device that has an integrated system for removing mucins and similar infectious secretions. The tracheal/endotracheal device has several channels. One channel delivers air to a patient's lungs. At least two other channels cooperate to deliver a mist of antiseptic ingredients to an area in the trachea and to suction away the mist and any mucins and secretions. The mist and bodily fluids captured by the suctioning channel are delivered to a collection vessel outside of the trachea.

4 Claims, 4 Drawing Sheets

(56) References Cited

U.S. PATENT DOCUMENTS

| | | | |
|---|---|---|---|
| 2004/0097801 A1* | 5/2004 | Mesallum | A61B 8/12 600/407 |
| 2005/0211245 A1* | 9/2005 | Smaldone | A61M 11/06 128/204.18 |
| 2007/0044807 A1* | 3/2007 | Madsen | A61M 16/0479 128/207.15 |
| 2009/0235935 A1 | 9/2009 | Pacey | |
| 2011/0146670 A1 | 6/2011 | Gallem | |

* cited by examiner

SYSTEM FOR REMOVING INFECTIOUS SECRETIONS

RELATED APPLICATIONS

This application claims the benefit of U.S. Provisional Patent Application Ser. No. 61/748,487 filed on Jan. 3, 2013—the contents of which are incorporated by reference herein.

FIELD OF THE INVENTION

The current invention relates to the field of medical equipment, more specifically to a tracheal or endotracheal breathing device which has an integrated system for removing secretions from a body site proximate to the endotracheal device.

BACKGROUND OF THE INVENTION

Ventilator Associated Pneumonia (VAP) is the second most common Hospital Acquired Infection (HAI) in the United States. Based on national health care statistics, it has been projected that between 9% and 25% of patients in intensive care units (ICU) will acquire pneumonia via mechanical ventilators while hospitalized and of these cases over 25% will die. The incremental cost of treating patients who become infected by assisted respiratory systems is significant and is estimated to be between $40,000 to $60,000 US dollars.

VAP principally affects patients who are intubated with endotracheal devices (typically in the ICU). In the process of intubation, a flexible tube is inserted into the trachea in order to maintain an open airway. Intubation is frequently performed on critically injured or critically ill patients to facilitate ventilation, including mechanical ventilation, of the lungs.

Passing a tube through the mouth (or nasal passage) and vocal cords into the trachea is the most common method of intubating. In a less common practice (used almost exclusively in emergency circumstances) a tracheotomy is performed where an incision on the external aspect of a patient's neck which forms a direct airway in the trachea and a tube is inserted therein.

After the trachea has been intubated, a balloon cuff is typically inflated just above the distal end of the tube—such that there is a tracheal/endotracheal tube segment superior to and inferior to the balloon. The balloon surrounds the outer perimeter of the tracheal/endotracheal tube and when inflated it contacts the inner walls of the trachea thereby securing the tube in place and protecting the lungs from receiving undesirable material such as stomach acid.

The primary cause of VAP is due to the flow of infected natural secretions (mucins) from the nasal passages and the oral region into the lungs. Nasal and oral secretions generally collect above the balloon in the subglottic region (superior to the balloon). If they are not appropriately drained, they can bypass the balloon and flow into the lungs.

This problem can be compounded with the flow back of infected mucins that are generated below the balloon (inferior region). Furthermore, mucins that are generated in or near the lungs and are expelled by coughing can accumulate below the balloon and flow back into the lungs exacerbating the infections.

While it is possible to isolate secretions in the subglottic region (the area between the balloon and the mouth) with a tracheal or endotracheal tube cuff- balloon, inevitably, unless these infected secretions are systematically and periodically removed, some will by-pass the balloon and flow into the lungs. Furthermore, as previously mentioned, secretions generated between the balloon and the lungs can accumulate and flow back into the lungs- In either case, these infected secretions enter the lungs causing pneumonia.

All current systems and practices deal with methods of removal of these secretions from the area superior to the balloon (the subglottic region, i.e., between the glottis and the balloon placement in the trachea). This is done manually via syringe or a regulator valve connected to wall suction. Accumulations of infectious mucus in this area is obvious and its removal relatively easy. However, in the area inferior to the balloon, any coughed up mucus or mucus that bypasses the balloon tends to drain into the lungs and is not visible.

Also, in areas where dry air impinges on the trachea, mucins can dry and adhere to the trachea. Such local adhesions may be visible through a stoma port on the trachea but not through an endotracheal tube placed through the oral cavity. Anecdotal reports from nurses who deal with patients in coma and on a stoma/tracheal tube have noted the problem of visible localized adhesion of the mucus to the trachea. Such localized mucin adhesion is generally invisible to the caregivers (with the possible exception of what can be seen through direct stoma type tracheal ports) and pose a difficulty in locating and removal without a complete lavage. If the caked on mucins can be seen, they must be removed since they can become infected and flow back into the lungs.

As noted above, infected mucus that drains into the lungs is invisible to the health care team and does not show itself until some type of pneumonia sets in with its associated complications. In any case, visible or not, infected mucins mixed with liquid can drain into the lungs and is the probable cause of Ventilator Associated Pneumonia (VAP) and must be removed from the tracheal region by the care giver.

It should be noted that patients on assisted breathing apparatus (coma/ICU) might also have other medical complications. Thus, the problem of humidifying the intake air and maintaining the health of the trachea may be overlooked. However, as the effects and cost of VAP increase, hospitals and health care teams are beginning to pay serious attention to this issue and it will probably become more prominent.

The issue of ventilator associated pneumonia (VAP) has been recognized as a serious health issue by the Agency for Healthcare Research and Quality (AHRQ) and at the Centers for Disease Control (CDC). Because this type pneumonia is the result of hospital inattention, effective in 2012, Medicare has decided not to reimburse hospitals on simple symptom definition. Reimbursement will be based on patient outcome and, thus, hospitals will be burdened with the cost of controlling VAP.

VAP cost and consequences are not light. In extreme cases of VAP, a total lung lavage is considered appropriate. Total lung lavage—i.e., Bronchoalveolar Lavage (BAL), is a medical procedure in which an antiseptic fluid is regionally circulated through the lung. BAL is typically performed to diagnose lung disease and has been used to diagnose infections in people on mechanical ventilators with pneumonia—i.e., VAP. This is a very expensive and complex procedure requiring extreme care to prevent morbidity and mortality and is generally not used on already compromised patients.

There is therefore a need in the art for a tracheal/endotracheal device that, both, maintains a patient's airway and which also actively cleanses surrounding tissue areas of harmful mucins, secretions or the like—thereby preventing a build-up of the same. Such system may reduce the incidence of infection and pneumonia and ultimately, it may reduce the incidence of death by VAP.

SUMMARY OF THE INVENTION

In order to address the problem of ventilator associated pneumonia (VAP) it is not sufficient to simply restrict the fluid to the area superior (i.e., above) the balloon, but a process and apparatus must be designed to remove the natural secretions inferior (i.e., below) to the balloon. Secretions below the balloon consist of mucins that by-pass the balloon as well as the secretions that are generated locally or are coughed up from the lungs.

As noted, restricting fluid extraction to the area superior to the balloon is only a partial solution. It is essential to address the entire area, both superior and inferior to the balloon, to achieve a successful solution to VAP. It is only by removal or neutralization of infected mucins in the complete tracheal region and preventing the flow of these infected fluids into the lungs that VAP can be controlled.

It should be noted that, other than bodily secretions (mucins), there are liquids that are introduced through the regularly required oral hygiene procedures such as brushing teeth, mouthwashes, etc., by the caregivers. These liquids cannot be completely removed from the oral cavity and some inevitably drain into the trachea and can get into the lungs causing complications.

The inventive tracheal/endotracheal tube set forth herein has an integrated pump that creates a fine antiseptic mist to liquefy mucins and a suctioning head to recapture the antiseptic mist along with mucins that were dislodged by the mist. The device is configured to simultaneously release antiseptic and to aspirate the mist/mucin mixture out of the trachea.

Two sets of cooperating tubes or channels are utilized to treat tissue areas superior to and inferior to the balloon. Each tube or channel has a first end that originates in an area that is external to a patient and a second end that terminates in an area within the trachea. Each set of cooperating tubes consists of at least one inlet tube and an outlet tube. The outlet tube is connected to a reservoir of antiseptic fluid or antiseptic active ingredients and a high pressure pump for creating a fine antiseptic mist. The outlet tube is used to deliver antiseptic fluid to a tissue area inside of the trachea. The cooperating inlet tube is connected to an aspirator for suctioning the antiseptic mist and delivering it to a canister or similar collection vessel outside of the trachea. Both cooperating tubes terminate in an area that is superior to the balloon. A second set of cooperating tubes (one for delivering antiseptic fluid and one for suctioning the same) terminate in an area that is inferior to the balloon.

As noted, the inventive tracheal tube apparatus consists of two independent devices, a high pressure pump that can insert a pulmonary compatible antiseptic liquid and an aspirator that can provide the necessary suction to remove all the secretions that accumulate in the area superior to the balloon and that adhere to the walls of the trachea in the area inferior to the balloon.

The inventive device may contain a stand-alone system that is exterior to the patient and is attached to an appropriately designed endotracheal/tracheal tube. It will be externally/internally powered to provide ease of use.

It should be noted that because of the proximity of the endotracheal tube to the left and right primary bronchus, it is imperative that no liquid be inserted in the region inferior to the balloon. Thus, in this particular region, the liquid antiseptic can only be in the form of a very fine mist that can be sprayed and simultaneously aspirated through the aspirator pump via a suction tube. Any liquids generated as the result of misting will similarly be suctioned using the aspirator pump.

DETAILED DESCRIPTION OF THE INVENTION

Figure 1:
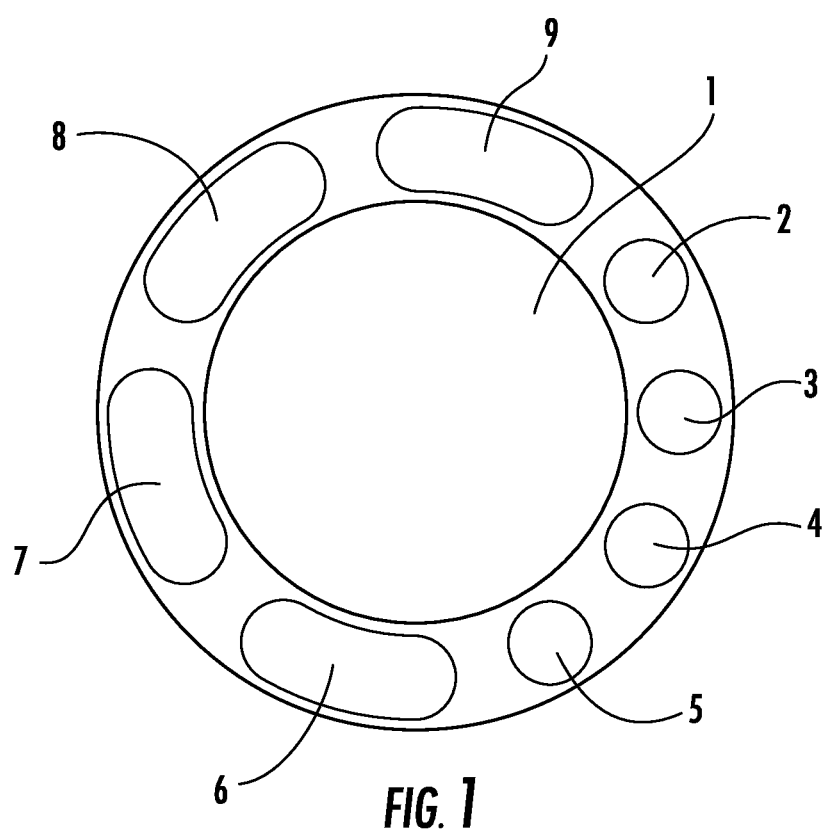
FIG. 1 is a schematic cross-sectional view of a tracheal/endotracheal tube showing various channels therein according to an embodiment of the invention.

Embodiments of the present invention will now be described with reference to the above-identified Drawings. However, the Drawings and the description herein of the invention are not intended to limit the scope of the invention. It will be understood that various modifications of the present description of the invention are possible without departing from the spirit of the invention. Also, features described herein may be omitted, additional features may be included, and/or features described herein may be combined in a manner different from the specific combinations recited herein, all without departing from the spirit of the invention.

As stated, intubation with a breathing tube is performed by inserting a flexible tube through a patient's oral (or nasal) cavity or by way of an incision in the patient's neck. By way of terminology, a tube that is inserted via the oral cavity is an endotracheal tube, whereas, a tube inserted through a stoma in a neck is a tracheal tube. It will be understood that the invention relates to both endotracheal tubes and tracheal tubes and term "tracheal" and "endotracheal" are used interchangeably herein. The inventive tracheal and endotracheal tube may be used with or without a ventilator (breathing machine).

The inventive tracheal/endotracheal tube consists of two principal systems—an external system and a cooperating internal tracheal/endotracheal device. Some of the external components consist of an aspirator with a pump in a single portable device. To the inventors' knowledge a portable mechanism with a high-pressure pump that can create a fine antiseptic mist to liquefy the mucins and simultaneously have the capability to aspirate the mixture out of the trachea does not exist in the medical pulmonary market today.

Some of the internal components consist of a special tracheal/endotracheal tube that cooperates with the external components to deliver humidifying antiseptic mist to the trachea while at the same time suctioning the contaminated mixture. Such a multifunction tube requires many auxiliary lumens for fluid injection and removal as well as directional and optical controls.

In a preferred embodiment of the invention, an aspirator is used to create negative pressure in order to draw a mist of antiseptic and/or other fluids and deliver to an external canister. The aspirator may be any vacuum suctioning or device, such as an impeller pump, a rotary vane pump or similar suctioning devices. Preferably, the aspirator 17 is capable of producing anywhere from 20 to 200 mmHg (4 psi) of pressure.

In one embodiment of the invention, the pump used to generate the mist is capable of generating up to 2100 mmHg of pressure. The pressure and flow rate control will be adjusted by the caregiver and will be adjusted to suit the requirements of each patient.

The tracheal/endotracheal device of the invention has a plurality of ports allowing for the simultaneous injection of a liquid or a fine humidifying mist and the aspiration of mucus. The terminal end of the tube, i.e., the part that is in the trachea, may have the ability to be directed by a mechanical means remote from the patient. One of the multiple channels could be used to run a fiber-optic device allowing observation of various points of the trachea.

The combination of the external components and the inventive tracheal device may be used by health care givers to provide RSMS "Respiratory Secretion Management System.

For the purpose of this application the terms channel, port, tube and lumen shall be equivalent and are defined as an enclosed tubular structure that will allow access from outside the body to inside the trachea.

For the purpose of this application the term cuff and balloon are equivalent and shall mean an inflatable sleeve that is placed on the exterior of the tracheal such that when inflated it separates the trachea into two regions. The first region is between the mouth and the balloon—the superior region. The second region is between the lungs and the balloon—the inferior region.

FIG. 1 shows a schematic cross sectional view of the tracheal/endotracheal tube specifying the usage of each various ports according to an embodiment of the invention. The tracheal tube will be extruded or molded from a biocompatible plastic type material preferably silicone. The molding or extrusion process allows for the formation of a multi lumen cross sections so that each lumen can be used for separate, non-interfering access.

It should be noted that the average male trachea has an approximate diameter of 21 mm and an average female trachea an approximate diameter of 18 mm. Thus, the maximum diameter of the tracheal/endotracheal tube cannot exceed 15 mm. The breathing Lumen 1 is designed for roughly 10 mm internal diameter. This is considered sufficient for maximum respiration rate of a patient.

Preferably, the average wall thickness is around 2.5 mm, which is sufficient for creation of multiple ports. All access ports will be completely encased in the wall of the tracheal tube as shown in FIG. 1. The function of each port in the tubular wall can be predefined and, for the purpose of this example, they are defined as noted below.

Lumen 1 is for respiratory function. It will attach to the external mechanical ventilator or assisted respiratory device.

Port 2 is be used to pass a bore scope with an illuminating fiber optic. Bore scopes with illuminating fiber optics with outside diameters of 1 mm are available on the commercial market. A 1.9 mm fiber optic cable may be used for viewing the trachea in an embodiment of the invention.

Port 3 is dedicated to inflation and deflation of the balloon. As the outer diameter of the tube is at most 15 mm and the minimum diameter of a trachea is probably in the range of 16.5 to 17 mm a balloon must be used to isolate the area in the upper part of the trachea from the lower part of the trachea (see also FIGS. 2 and 3). Once the tube is in place the balloon is inflated to seal the area and reduce the by-pass of all fluids between the two regions. In order to remove the tracheal tube, it is necessary to deflate the same balloon. Inflation and deflation is by means of the same port 3 shown in FIG. 1. Maintaining correct balloon pressure is necessary to restrict contaminated liquid from flowing around the balloon and into the lungs. (Typically the balloon pressure is maintained and periodically checked. In the Pump/Aspirator device a controller will automatically check the balloon pressure and make sure that the seal between the tracheal wall and the balloon is consistent.)

Port 4 and Port 5 will be used to run the wires to the tip of the flexible tracheal tube thus providing directional control of the tip to the caregiver. In normal operation the wires will be pre-adjusted to direct tip toward the center of the trachea in the direction of the lungs.

Port 6 is for the injection of either antiseptic mist or a liquid to neutralize any infection and reduce the viscosity of the mucus to allow its suction and removal form the area superior to the balloon. It will be understood that any of various liquids/and or gases may be delivered via port 6 (or port 8) to a patient's trachea in embodiments of the invention.

Port 7 is to drain the mixture of antiseptic mist and/or fluid and mucus from the region superior to the balloon.

Port 8 is for the introduction of an antiseptic mist to the area of the trachea inferior (i.e., toward the lungs). At its outlet there will be an atomizing nozzle 8.1 (FIGS. 2 and 3) that will create a fine antiseptic cloud. The cloud can be expelled from the area through Lumen 1 by normal breathing or suction directly by Port 9.

Port 9 is for the suction and removal of any mist or mucus from the area inferior to the balloon. The suction on this port will be synchronized with injection from Port 8 and the respiration cycle dictated by the mechanical ventilator attached to Lumen 1. The guide wires in Ports 4 and 5 as shown in FIGS. 2 and 3 can direct the tip of the tube.

It should be noted that this is an outline of the port usage and that the tracheal/endotracheal tube can be modified for other use. Furthermore, the circular cross section shown is for visual example. These ports may be molded or extruded in various forms such as triangular or square or other multi sided shapes in order to facilitate the passage of equipment or fluids into the tracheal area.

Figure 2:
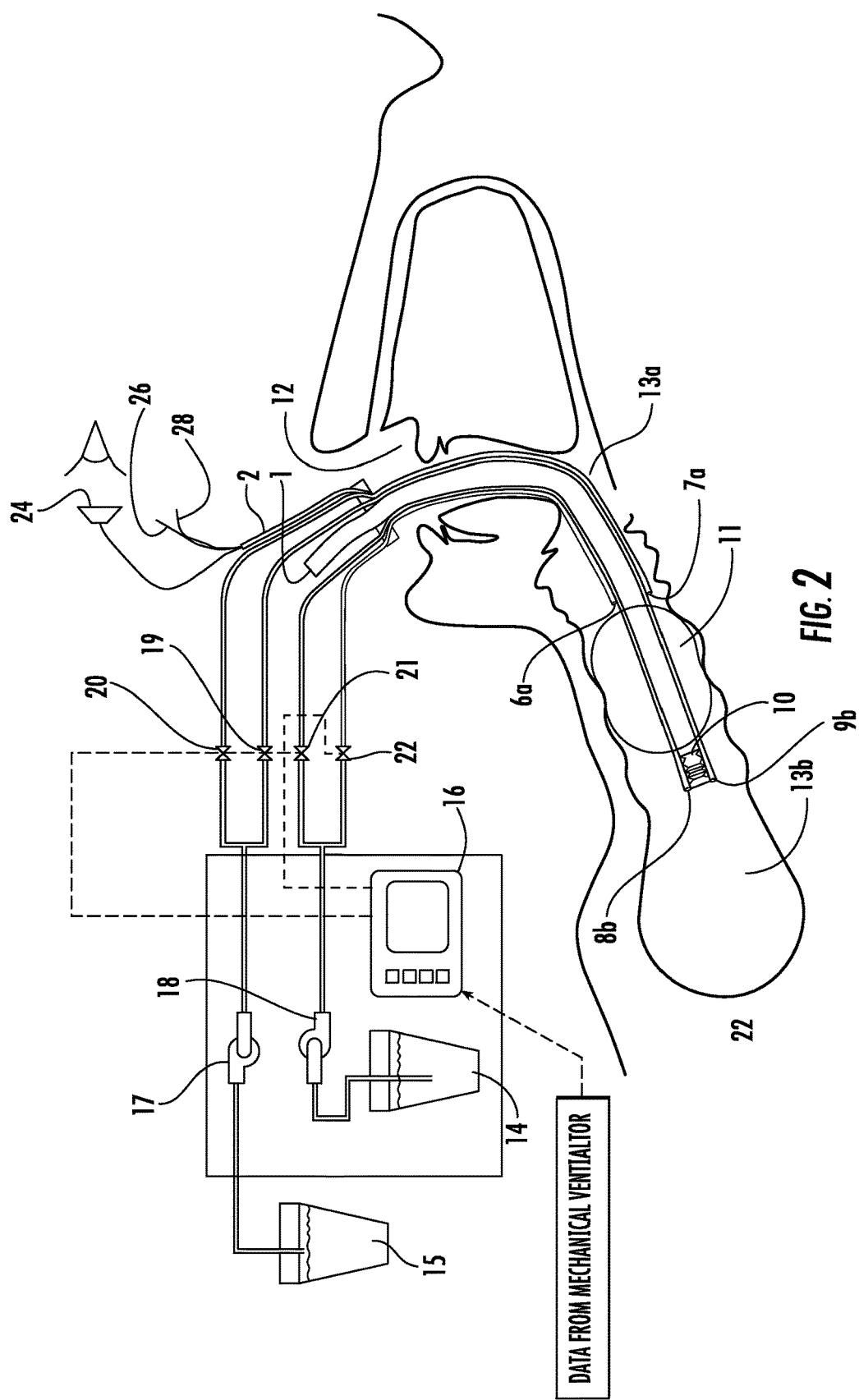
FIG. 2 is a schematic side cross-sectional view of an endotracheal device inserted through a patient's mouth according to an embodiment of the invention.
Figure 3:
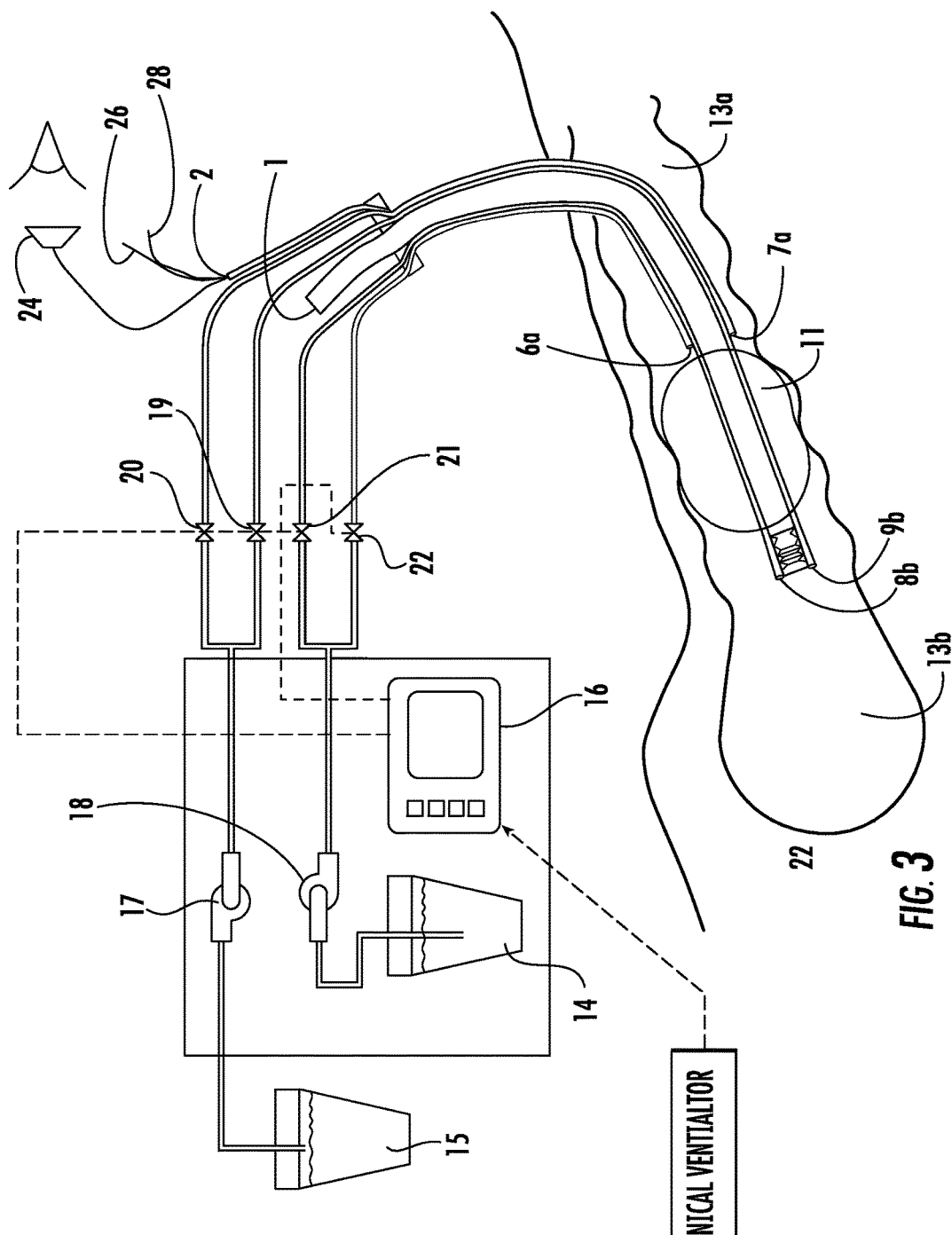
FIG. 3 is a side schematic cross-sectional view of a tracheal device inserted through a stoma in a patient's neck according to an embodiment of the invention.

FIG. 2 shows an endotracheal system in which the tube is placed into the trachea orally. In this figure the oral cavity 12 is separated from the lungs 22 by the balloon 11 of the endotracheal tube.

As previously noted in FIG. 1, lumen 1 is for the passage of air and assistance to breathing, usually, via an external mechanical ventilator. All other ports on the tracheal tube have been identified in FIG. 1 and the attachment of the endotracheal tube to the pump/aspirator is shown.

A bore scope 24 may be inserted through the appropriate channel, e.g. Port 2 on the endotracheal tube to allow the caregiver to get a direct optical view of the immediate region of the trachea inferior to the balloon shown as region 13b. Directional control of the tracheal tubes is by the two guide wires 26, 28 that are attached asymmetrically to the inferior tip of the tracheal tube. In-line bellows 10 allow the tip of the tracheal tube to move in multiple directions.

The bellows are placed in the inferior region 13b of the trachea (proximal to the lungs) and below the balloon 11. Also in this region will be the atomizer nozzle 8b allowing antiseptic mist to be sprayed in region 13b thus reducing the possibility of VAP.

The liquids generated by the antiseptic mist will be aspirated via suction head 9b. Suction from an external pump is activated prior to introduction of mist through nozzle 8b; thus any generated fluid will be aspirated and no fluid will accidentally flow into the lungs.

The mist generated by nozzle 8b can be removed by synchronizing the patient expiration through lumen 1 with the mechanical ventilator. Synchronizing the action of aspirator 17 and pump 18 with the mechanical ventilator is important. The spraying of the aerosol mist from nozzle 8b must coincide with the expulsion of air from the lungs through lumen 1. This activity will be sequenced using the electronic controller 16.

In the superior region 13a, above the balloon 11 there are two terminal ends 6a, 7a of channels 6 and 7. The anti-viscosity and antiseptic fluid will be withdrawn from container 14 by pump 18 and injected via valve 21 through Port 6 and out of nozzle 6a into region 13a.

Port 7a is used in conjunction with aspirator 17 to collect the contaminated fluid and store it in container 15. Suction control will be provided with valve 19. In region 13a, superior to the balloon, introduction of fluids is not restricted however, adequate removal is critical since excess fluids can bypass balloon 11 and flow into lungs 22.

Cooperating tubes 8 and 9 inferior to the balloon 11 operate in substantially the same manner as described with respected to cooperating tubes 6 and 7.

The functions and timing of the pump 18 and aspirator 17 operations are controlled by an electronic controller 16. In a preferred embodiment, controller 16 comprises a computer that is used to control operations, execute routines and store data. The computer may comprise at least one or more processors and memory storage devices. The computer also may receive a number of inputs and outputs for communicating information externally.

The computer operates under the control of an operating system and software applications, components and programs that execute the routines and systems described herein. In general, the routines executed to implement the embodiments of the invention, whether implemented as part of an operating system or a specific application, component, program, object, module or sequence of instructions will be referred to herein as the "software" or "the controller."

The software is programmed to activate the aspirator 17 used to suction mist prior to activating the pump 18 that delivers the mist to the trachea. The controller also receives input via a mechanical or electrical signal from the ventilator (not shown) that will allow controlled delivery of atomized antiseptic mist via nozzle 8b into inferior region 13b. In this manner, the controller is programmed to sequence the operation of all components of the device for injection of antiseptic and retrieval mucus and other liquid and mist from the tracheal area. In the case where a tracheal tube is connected to an external ventilator, the controller also will time the release of any mist to occur during a period that the ventilator is applying negative pressure to the patient's lung.

Valves 19 and 22 will control the fluid injection and removal from the area superior to the balloon. Valve 19 from aspirator 17 and valve 21 from pump 18 will be interlinked so that they will operate in conjunction. This will assure that any fluid that is used for the lavage, mucin removal and/or the by-product of oral hygiene will be removed appropriately. Aspirator 17 will dispose any collected fluid into container 15.

Valve 21 will be used for aerosol spray into the region inferior to the balloon. It should be noted that pump 18 will have the required power to completely atomize any antiseptic fluid withdrawn from container 14 and moved through port 8 to the nozzle 8b. The aspirator 17 controlled by valve 20 will be activated prior to operation of pump 18 such that suction will begin prior to mist injection in order to assure full removal of any liquefied secretions. It will be understood by those of ordinary skill in the art that various means of creating a mist are possible in different embodiments of the invention. For example, as an alternative to an aerosol spray—antiseptic fluid may be vaporized and delivered in gas phase. In other embodiments, fine droplets of antiseptic is delivered through micro pores at the terminal end of channel 6 or 8.

The mechanical ventilator (not shown) will be synchronized with the pump such that the spray will only be active when the ventilator is providing negative pressure to the lungs. At no time will the pump 18 spray any aerosol into the lungs unless the aspirator 17 is fully active and the mechanical ventilator is functioning in an exhalation mode.

FIG. 3 shows the inventive tracheal device that is inserted into a stoma in a patient's neck. The device in FIG. 3 operates in the same manner as described with respect to FIG. 2.

Figure 4:
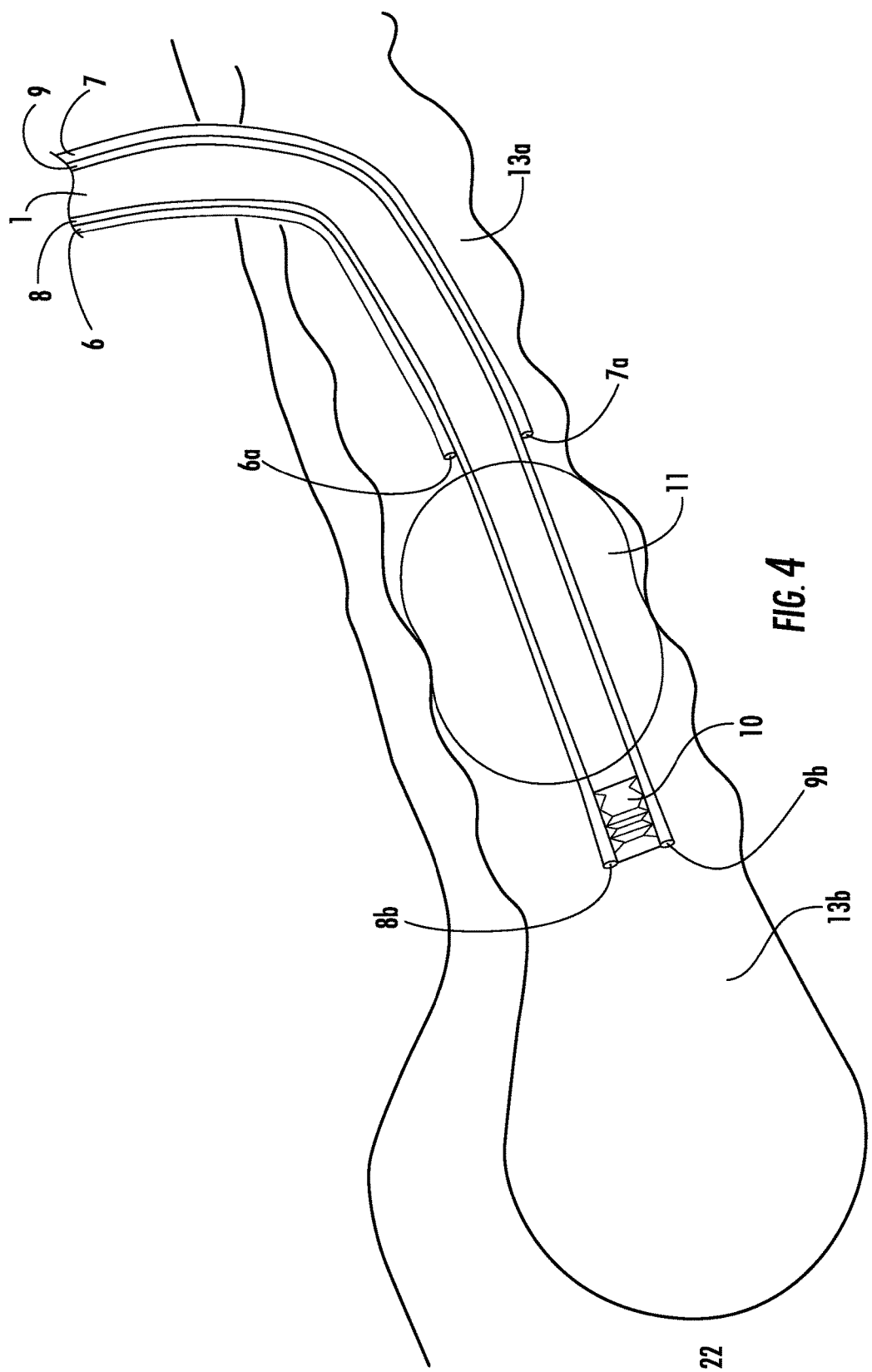
FIG. 4 is an enlarged schematic cross-sectional view of a segment of a tracheal/endotracheal device inserted into a trachea according to an embodiment of the invention.

FIG. 4 is an enlarged view of the segment of the tracheal device that is inserted into the patient's trachea. The terminal ends of two cooperating sets of channels are shown. Channels 6a and 7a terminate in the area superior to the balloon 11 and channels 8b and 9b terminate in area that is inferior to the balloon. The terminal end 6a of channel 6 is provided with a nozzle or similar flow control device for emitting a mist or fine spray. Terminal end 7a of channel 7 is a suctioning head for suctioning any fluid or mist released by nozzle 6a. The mist, containing a mixture of antiseptic, mucin or similar bodily fluids are delivered to canister 15 through channel 7.

Similarly, cooperating channels 8 and 9 terminate in an area that is inferior to the balloon. The terminal end 8b of channel 8 is provided with a nozzle or similar flow control device for emitting a mist or fine spray. Terminal end 9b of channel 9 is a suctioning head for suctioning any fluid or mist released by nozzle 8b. The mist, containing a mixture of antiseptic, mucin or similar bodily fluids are delivered to canister 15 through channel 9.

Nozzle 8b and suction head 9b are disposed in close enough proximity to allow suctioning of substantially any mist that is released from nozzle 8b. The same is true for nozzle 6a and suction head 7a respectively.

Having described this invention with regard to specific embodiments, it is to be understood that the description is not meant as a limitation since further modifications and variations may be apparent or may suggest themselves to those skilled in the art. It is intended that the present application cover all such modifications and variations.

What is claimed is:

1. A method of decreasing a probability of Ventilator Associated Pneumonia, said method comprising the steps of:
   a. inserting a tracheal/endotracheal device into the trachea of a patient;
   b. inflating a balloon that surrounds a segment of said tracheal/endotracheal device,
   whereby a segment of said tracheal/endotracheal device is disposed inferior to said balloon and a segment of said tracheal/endotracheal device is disposed superior to said balloon
   c. delivering a mist through a port in said tracheal/endotracheal device, said mist being released in and delivered to the trachea, in an area that is inferior to said balloon;

d. simultaneously with the delivery step c, providing suction to capture mist or fluid from said inferior area in said trachea; and e. delivering captured mist or fluid to a collection vessel that is disposed outside of said trachea, wherein the provision of suction commences prior to the delivery of the mist and wherein the delivery of the mist is synchronized with the expulsion of air from the patient's lungs.

2. The method of claim 1, whereby said mist comprises antiseptic ingredients.

3. The method of claim 1, wherein the provision of suction prior to the delivery of the mist is effected by an electronic controller having control of a pump and an aspirator.

4. The method of claim 2, wherein the provision of suction prior to the delivery of the mist is effected by an electronic controller having control of a pump and an aspirator.

\* \* \* \* \*